United States Patent [19]

Yapor

[11] Patent Number: 5,391,178
[45] Date of Patent: Feb. 21, 1995

[54] CEREBRAL DILATOR

[76] Inventor: Wesley Yapor, 5525 S. Keeler, Chicago, Ill. 60629

[21] Appl. No.: 196,291

[22] Filed: Feb. 14, 1994

[51] Int. Cl.$^6$ .......................................... A61M 25/00
[52] U.S. Cl. ................................................. 606/192
[58] Field of Search ............................ 604/96, 101; 606/191–194, 198, 197, 196, 195

[56] References Cited

U.S. PATENT DOCUMENTS

| | | | |
|---|---|---|---|
| 3,613,684 | 10/1971 | Sheridan | 128/347 |
| 3,882,852 | 5/1975 | Sinnreich | 128/344 |
| 4,312,353 | 1/1982 | Shahbabian | 128/344 |
| 4,684,363 | 8/1987 | Ari | 128/349 |
| 5,171,221 | 12/1992 | Samson | 604/96 |
| 5,188,630 | 2/1993 | Christoudias | 606/191 |
| 5,275,611 | 1/1994 | Behl | 604/264 |
| 5,290,230 | 5/1994 | Dinsroth et al. | 604/96 |

*Primary Examiner*—C. Fred Rosenbaum
*Assistant Examiner*—Manuel Mendez
*Attorney, Agent, or Firm*—Leydig, Voit & Mayer, Ltd.

[57] ABSTRACT

A surgical dilator for dilation of cerebral tissue, having an outer needle, an inner needle insertable into the outer needle and an expandable sac attached to the outer needle, which permits access to a tumor, cerebral ventricle or other tissue by dilating the cerebral tissue in its path and indicates when such tumor, ventricle or other tissue has been entered by the release of fluid through the outer needle. Also, a method of verifying entry into a tumor, ventricle or other tissue and creating a bloodless opening to such tumor, ventricle or other tissue in cerebral tissue utilizing the surgical dilator.

30 Claims, 1 Drawing Sheet

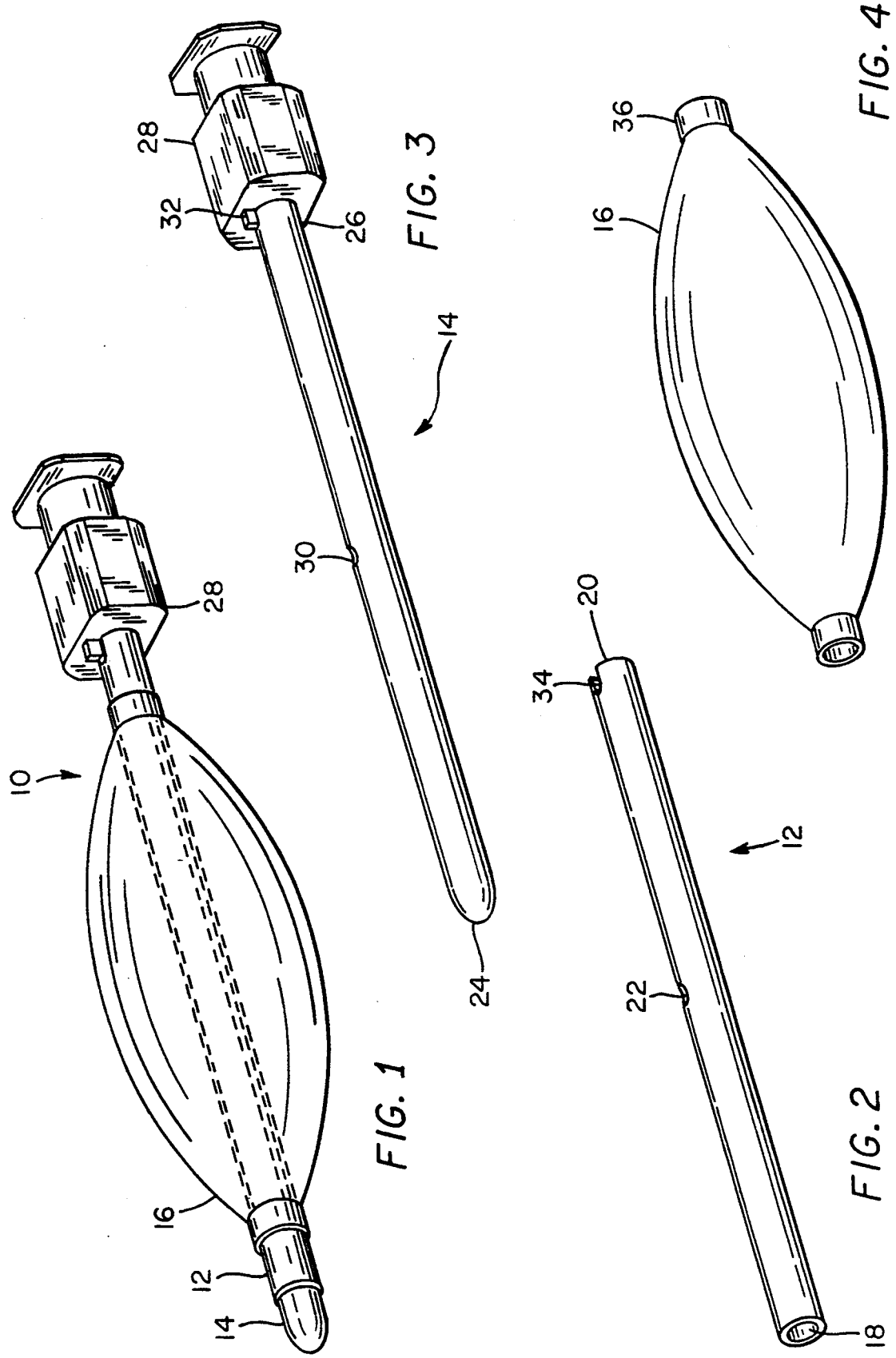

CEREBRAL DILATOR

TECHNICAL FIELD OF THE INVENTION

The present invention is directed generally to a surgical dilator and relates specifically to a cerebral dilator for use in neurosurgery.

BACKGROUND OF THE INVENTION

Dilators of various types have been used in the past and are still used today for an assortment of purposes.

Catheters account for a large amount of the instruments used for dilation today. Balloon catheters are commonly used in angiography, angioplasty, angioocclusion, endoscopy, and cervix and uterus examination and surgical procedures. These balloon catheters are simply catheters having a distal balloon that can be inflated at a target site, i.e., a blood vessel. Such catheters are described in U.S. Pat. Nos. 3,882,852, 4,684,363, 5,171,221, and 5,188,630.

Trocar catheters are generally used in emergency situations, and, in particular, are used for insertion into the chest or stomach wall of a patient for withdrawal of fluid within a body cavity, rather than for dilation of body tissue. Such catheters are described in U.S. Pat. No. 3,613,684.

Balloon and trocar catheters, while useful in many surgical procedures, are generally not particularly suited to neurosurgery. Nerve cells or neurons receive, conduct and transmit signals. Communication depends upon an electrical disturbance produced in one part of the cell which spreads to other parts of the cell, and neurons are woven together to form circuits of great complexity. The nerve bundles in the brain are surrounded by connective or supporting tissue called glial cells. The nerve tissue is generally stronger and more resistant to rupture than connective tissue, but care must still be exercised with respect to nerve tissue to avoid damage thereto. In the past, to access an internal section of the brain, it was necessary to cut an opening in the brain with a scalpel. In the process of creating a hole large enough to permit access to a tumor, an extraordinary amount of nerve tissue had to be severed, thereby creating permanent injury to the brain.

U.S. Pat. No. 4,312,353 describes a method for using a catheter to permit surgical operations without the use of a scalpel to cut away tissue. The catheter described is a stylette surrounded by an inflatable sac. Upon insertion into the brain, the sac may be inflated to push aside the connective tissue creating an opening for surgery. The main problem with this catheter is that it is unable to determine when the catheter has been inserted to the desired target prior to inflating the expandable sac. This can result in unnecessary damage to neurons and connective tissue. Further, there is also no method to remove fluid which may fill and block the newly created opening.

A need therefore exists for a dilator which can verify entry into a cerebral ventricle, cystic tumor, abscess, hematoma or any fluid filled cavity. A further need exists for a dilator which can remove and drain fluid which may block the newly created opening in brain connective tissue, thereby creating a bloodless tract through which surgery may be performed. The foregoing and other needs are satisfied by the present invention and will be apparent from the description of the invention provided herein.

SUMMARY OF THE INVENTION

The present invention provides a dilator assembly comprising an outer needle having a first aperture through which fluid may pass, and an inner needle which is insertable into the outer needle having a closed distal end and a second aperture alignable with the first aperture when the inner needle is fully inserted into the outer needle. The distal end of the inner needle forms a seal with the outer needle when fully inserted. The proximal end of the inner needle has a means for connecting to a fluid source, such as a syringe. An expandable sac or balloon is attached to the outer needle intermediate the proximal and distal ends.

The present invention also provides a method of verifying entry into a cerebral ventricle, cystic tumor, abscess, hematoma or any fluid filled cerebral cavity and creating a bloodless opening utilizing the dilator assembly described above. The dilator assembly is inserted into cerebral tissue with the inner needle inserted into the outer needle and the expandable sac deflated. The inner needle is removed from the outer needle a sufficient amount to permit drainage of fluid through the outer needle. Such drainage verifies entry into the desired tumor or ventricle. After such verification, the inner needle is reinserted, and an inflation fluid is passed through the inner needle and the apertures of both needles to inflate the expandable sac. The inflation fluid may then be released from the sac and the dilator assembly, thereby leaving an opening in the cerebral tissue to the tumor or ventricle of interest.

BRIEF DESCRIPTION OF THE DRAWINGS

FIG. 1 depicts a perspective view of the dilator assembly of the present invention having the inner needle fully inserted into the outer needle and the expandable sac inflated.

FIG. 2 depicts a perspective view of the outer needle of the dilator assembly of the present invention.

FIG. 3 depicts a perspective view of the inner needle of the dilator assembly of the present invention.

FIG. 4 depicts a perspective view of the expandable sac of the dilator assembly of the present invention.

DETAILED DESCRIPTION OF THE INVENTION

The invention may best be understood with reference to the accompanying drawings wherein illustrative embodiments are shown and in the following detailed description of the preferred embodiments.

As shown in FIG. 1, the dilator assembly 10 of the present invention in its simplest form comprises an outer needle 12, an inner needle 14, and an expandable sac 16. The dilator assembly can be of any suitable dimensions and prepared from any suitable materials. The preferred dimensions and materials of the dilator assembly are set forth herein in describing the dilator assembly of the invention.

FIG. 2 depicts the outer needle of the dilator assembly. The outer needle 12 is hollow and has an open distal end 18 as well as an open proximal end 20. Preferably, the distal end 18 is tapered. The diameter of the outer needle 12 is about 2 to 5 mm, preferably about 2 to 3 mm. Moreover, the length of the outer needle 12 is about 80 to 150 mm, preferably about 100 to 120 mm.

The outer needle 12 should have a first aperture 22 through which fluid may pass. The diameter of the aperture 22 is about 0.5 mm to about 1.0 mm, preferably about 0.8 mm.

The inner needle 14, as depicted in FIG. 3, should have a diameter small enough to fit inside the outer needle 12. Therefore, the diameter will be preferably about 1.0 mm to about 4.5 mm, more preferably about 1.5 mm to about 3.0 mm, depending upon the diameter of the outer needle 12. The inner needle 14 is fully insertable into the outer needle 12. The inner needle 14 has a closed distal end 24 and a proximal end 26 which has a connecting means for connecting to a fluid source 28. The means for connecting to a fluid source 28 may be of any suitable construction and is preferably a luer lock connection which is depicted in FIGS. 1 and 2. When the inner needle 14 is fully inserted into the outer needle 12, a seal is formed between the inner needle 14 and the outer needle 12 at the distal ends 18, 24.

The inner needle 14 has a second aperture 30 having a diameter from about 0.5 mm to about 1.0 mm, preferably about 0.5 mm to about 0.9 mm, and most preferably having the same size as the first aperture 22. The second aperture 30 is preferably aligned with the first aperture 22 of the outer needle 12 to more easily permit fluid to pass through. Accomplishment of such alignment may be achieved by any suitable means, and is preferably achieved with a luer lock connection. If a luer lock connection is used, a groove 32 in the inner needle 14 aligns with a notch 34 on the outer needle 12 and provides alignment of the first aperture 22 and the second aperture 30.

The inner needle 14 and outer needle 12 of the dilator assembly 10 may have multiple apertures which are also preferably aligned for easy passage of fluid.

Both the inner needle 14 and outer needle 12 may be formed from metal, such as stainless steel, a nondistensible polymer such as polyethylene, polyester, polypropylene, polyamide, and polyvinyl chloride, or glass. The preferred material is a plastic which can be formed into the desired shape and dimensions by any suitable means, such as extrusion, dipping, injection molding, centrifugal casting or the like. If a plastic is used, fillers and pigments may be included to achieve a translucent or opaque dilator assembly 10 rather than a transparent dilator assembly 10. The inner needle 14 and outer needle 12 may be formed of the same or different materials.

FIG. 4 depicts an expandable sac 16 which is attachably sealed to the outer needle 12 intermediate the proximal end 20 and distal end 18. The expandable sac 16 may be attachably sealed to the outer needle 12 by one or more fluid tight sealing means 36 to prevent the leakage of fluid from the expandable sac 16. Although not critical, the distal end 18 preferably extends beyond the point of attachment of the expandable sac 16 by about 2 mm to about 10 mm, preferably by about 5 mm.

The expandable sac 16 is preferably a balloon and may be made of a suitable polymeric material, such as polyethylene. The expandable sac 16, as attached to the outer needle 12, can be of any suitable dimensions, e.g., about 7 cm to about 12 cm long, preferably 10 cm long. When the sac 16 is inflated, it will typically have a diameter between about 10 mm and about 30 mm, preferably about 15 mm to about 20 mm.

To inflate the expandable sac 16, a fluid source is necessary. This may include a syringe, intravenous tubing connected to a syringe or arterial tubing connected to a syringe. The luer lock connection operates as a means for receiving a fluid source, such as a syringe (not shown).

The fluid which may be used to expand the sac 16 may be a sterile non-noxious liquid, such as water or a saline solution, and is preferably air.

The dilator assembly 10 of the present invention is a surgical device that may be sterilized by any available method, such as by exposure to ethylene oxide vapors, gamma radiation or similar techniques, and used multiple times. However, in a preferred embodiment, the dilator assembly 10 is formed from plastic and is disposable.

The method of the present invention involves creating a bloodless opening in human tissue, namely cerebral tissue, by using the present inventive dilator assembly 10.

Initially, an opening must be created in the skull to access cerebral tissue. After an opening has been formed, the dilator assembly 10 of the present invention is inserted into cerebral tissue, preferably in the direction of the targeted tissue. Generally, the dilator assembly 10 will tend to take the path of least resistance preventing great damage to the cerebral tissue. Although some damage may occur, such damage is minimal as compared to utilizing a scalpel to cut away cerebral tissue. Upon suitable insertion, the inner needle 14 is inserted into the outer needle 12, and the expandable sac 16 is deflated.

After the dilator assembly 10 is inserted, the inner needle 14 is removed from the outer needle 12. Such removal is critical and permits the drainage of cerebral or tumor fluid, pus or blood through the outer needle 12. The drainage of fluid, pus or blood indicates entry into the targeted tissue, usually a cerebral ventricle, cystic tumor, abscess, hematoma or fluid filled cavity, before inflation of the expandable sac 16.

After drainage of the fluid and verification of entry into the cerebral ventricle, cystic tumor, abscess, hematoma or fluid filled cavity, the inner needle 14 is re-inserted into the outer needle 12. Upon re-insertion, the first aperture 22 and second aperture 30 are in alignment to permit ease of fluid flow from the inner needle 14 into the expandable sac 16.

After the first and second apertures 22, 30 are aligned, an inflation fluid may be passed through the inner needle 14, the second aperture 30 and the first aperture 22, into the expandable sac 16. Such inflation is preferably performed slowly and results in the pushing aside of connective tissue in the brain. The inflation liquid is left in the expandable sac 16 for a suitable period of time, e.g., for about 10 to about 20 seconds, preferably about 10 to 15 seconds. The inflation fluid is then released from the expandable sac 16, thereby deflating the expandable sac 16. At this point, the dilator assembly 10 may be removed from the cerebral tissue in its entirety.

After a bloodless opening has been created, it may be desirable to use retractors or some other device to hold the tissue in place during the surgery.

In some instances, before removing the dilator assembly 10, it may be preferable to expand and deflate the expandable sac 16 repeatedly while increasing the amount of inflation fluid passed into the expandable sac 16 on each repetition. Such repetition may result in less damage to surrounding connective tissue than would occur if the expandable sac 16 is expanded at one time to the greatest amount desired.

All of the references cited herein are hereby incorporated by reference in their entireties.

While this invention has been described with an emphasis upon preferred embodiments, it will be obvious to those of ordinary skill in the art that variations in the preferred dilator and method may be used and that it is intended that the invention may be practiced otherwise than as specifically described herein. Accordingly, this invention includes all modifications encompassed within the spirit and scope of the invention as defined by the following claims.

What is claimed is:

1. A dilator assembly for creation of a bloodless opening comprising:
   (a) an outer needle having an open distal end, an open proximal end and a first aperture through which fluid may pass;
   (b) an inner needle which is insertable into said outer needle, said inner needle having a closed distal end, a proximal end, and a second aperture alignable with said first aperture when said inner needle is fully inserted into said outer needle, said distal end of said inner needle forming a seal with the outer needle when fully inserted, and said proximal end of said inner needle having a means for connecting to a fluid source; and
   (c) an expandable sac attached to said outer needle intermediate said proximal end and said distal end.

2. The dilator assembly according to claim 1, wherein said means for connecting to a fluid source is a luer lock connection.

3. The dilator assembly of claim 1, which dilator assembly further comprises a fluid source.

4. The dilator assembly of claims 3, wherein said fluid source is selected from the group consisting of a syringe, intravenous tubing and arterial tubing.

5. The dilator assembly according to claim 1, wherein said distal end of said outer needle is tapered.

6. The dilator assembly according to claim 1, wherein said dilator assembly further comprises a groove on said proximal end of said outer needle and a notch on said proximal end of said inner needle insertable into said groove on said outer needle to align said first and second apertures.

7. The dilator assembly according to claim 1, wherein the outer needle has a diameter of about 2 to 5 mm.

8. The dilator assembly according to claim 1, wherein the inner needle has a diameter of about 1.0 to 4.5 mm and is not greater than the diameter of the outer needle.

9. The dilator assembly according to claim 1, wherein said inner needle comprises a material selected from the group consisting of metal, a nondistensible polymer, and glass.

10. The dilator assembly of claim 9, wherein said inner needle comprises a nondistensible polymer.

11. The dilator assembly according to claim 9, wherein said inner needle comprises stainless steel.

12. The dilator assembly according to claim 10, wherein said nondistensible polymer is selected from the group consisting of polyethylene, polyester, polypropylene, polyamide, and polyvinyl chloride.

13. The dilator assembly according to claim 1, wherein said outer needle comprises a material selected from the group consisting of metal, a nondistensible polymer, and glass.

14. The dilator assembly according to claim 13, wherein said outer needle comprises a nondistensible polymer.

15. The dilator assembly according to claim 13, wherein said outer needle comprises stainless steel.

16. The dilator assembly according to claim 14, wherein said nondistensible polymer is selected from the group consisting of polyethylene, polyester, polypropylene, polyamide, and polyvinyl chloride.

17. The dilator assembly according to claim 1, wherein said expandable sac comprises a polymeric material.

18. The dilator assembly according to claim 17, wherein said polymeric material comprises polyethylene.

19. The dilator assembly according to claim 1, wherein said expandable sac is about 7 cm to about 12 cm long.

20. The dilator assembly according to claim 1, wherein said expandable sac is about 10 cm long.

21. The dilator assembly according to claim 1, wherein said dilator assembly is disposable.

22. A method for creating a bloodless opening in cerebral tissue comprising:
   (a) providing a dilator assembly comprising an outer needle having an open distal end, an open proximal end and a first aperture through which fluid may pass; an inner needle which is insertable into said outer needle, said inner needle having a closed distal end, a proximal end, and a second aperture alignable with said first aperture when said inner needle is fully inserted into said outer needle, said distal end forming a seal with the outer needle when fully inserted, and said proximal end having a means for connecting to a fluid source; and an expandable sac attached to said outer needle intermediate said proximal end and said distal end;
   (b) inserting into cerebral tissue said dilator assembly with said inner needle inserted into said outer needle and said expandable sac deflated;
   (c) removing said inner needle from said outer needle sufficient to permit drainage of fluid through the outer needle;
   (d) reinserting said inner needle into said outer needle with said first aperture and said second aperture in alignment;
   (e) passing an inflation fluid through said inner needle, second aperture and first aperture to inflate said expandable sac;
   (f) releasing said inflation fluid from said expandable sac deflating said sac; and
   (g) removing said dilator assembly from said cerebral tissue.

23. The method according to claim 22, wherein said drainage of fluid through said outer needle verifies entry into targeted tissue.

24. The method according to claim 23, wherein said targeted tissue is any fluid-filled cerebral cavity.

25. The method according to claim 23, wherein said targeted tissue is selected from the group-consisting of a cystic tumor, cerebral ventricle, absess, and hematoma.

26. The method according to claim 22, wherein the inflation fluid remains in the expandable sac for about 10 to 20 seconds.

27. The method according to claim 22, wherein said expandable sac can be expanded up to about 30 mm in diameter.

28. The method according to claim 22, wherein passing an inflation liquid through said inner needle, first aperture and second aperture to inflate said expandable sac and releasing said inflation liquid from said expandable sac is repeated while increasing the amount of inflation liquid in the expandable sac on each repetition.

29. A method for determining entry of a dilator assembly into a brain tumor comprising:

(a) providing a dilator assembly comprising an outer needle having an open distal end, an open proximal end and a first aperture through which fluid may pass; an inner needle which is insertable into said outer needle, said inner needle having a closed distal end, a proximal end, and a second aperture alignable with said first aperture when said inner needle is fully inserted into said outer needle, said distal end forming a seal with the outer needle when fully inserted, and said proximal end having a means for connecting to a fluid source; and an expandable sac attached to said outer needle intermediate said proximal end and said distal end;

(b) inserting into cerebral tissue said dilator assembly with said inner needle inserted into said outer needle and said expandable sac deflated; and (c) removing said inner needle from said outer needle sufficient to permit drainage of fluid through the outer needle; said drainage indicating entry into said tumor.

30. A method for removing fluid from cerebral tissue comprising:

(a) providing a dilator assembly comprising an outer needle having an open distal end, an open proximal end and a first aperture through which fluid may pass; an inner needle which is insertable into said outer needle, said inner needle having a closed distal end, a proximal end, and a second aperture alignable with said first aperture when said inner needle is fully inserted into said outer needle, said distal end forming a seal with the outer needle when fully inserted, and said proximal end having a means for connecting to a fluid source; and an expandable sac attached to said outer needle intermediate said proximal end and said distal end;

(b) inserting into cerebral tissue said dilator assembly with said inner needle inserted into said outer needle and said expandable sac deflated; and (c) removing said inner needle from said outer needle sufficient to permit drainage of fluid through the outer needle.

* * * * *